(12) United States Patent
Singh et al.

(10) Patent No.: US 6,436,417 B1
(45) Date of Patent: Aug. 20, 2002

(54) ACNE TREATMENT COMPOSITIONS

(75) Inventors: Mohinder Singh, Naperville; Michael A. Wojcik, Plainfield, both of IL (US)

(73) Assignee: Blistex Inc., Oak Brook, IL (US)

( * ) Notice: Subject to any disclaimer, the term of this patent is extended or adjusted under 35 U.S.C. 154(b) by 0 days.

(21) Appl. No.: 09/888,766

(22) Filed: Jun. 25, 2001

(51) Int. Cl.[7] .......................... A61K 7/00; A61K 31/19; A61K 7/24; A61K 25/02; A61K 7/48

(52) U.S. Cl. ..................... 424/401; 424/78.02; 424/443; 424/446; 424/DIG. 6; 424/55; 514/836; 514/848; 514/859; 514/887

(58) Field of Search .................. 424/401, 78.02, 424/443, 446, DIG. 6, 55; 514/859, 848, 887, 836

(56) References Cited

U.S. PATENT DOCUMENTS

| | | | | |
|---|---|---|---|---|
| 4,488,989 A | * | 12/1984 | Lamberti | 252/541 |
| 4,891,227 A | * | 1/1990 | Thaman et al. | 424/443 |
| 5,549,888 A | * | 8/1996 | Venkateswaran | 424/78.02 |

OTHER PUBLICATIONS

International Cosmetic Ingredient Dictionary and Handbook, 1997, The Cosmetic, Toiletry, and Fragrance Association, Seventh Edition, vol. 1–3, pp. 70, 73, 488, 1128, 1251, 1611, 1626.*

* cited by examiner

Primary Examiner—Frederick Krass
Assistant Examiner—Clinton Ostrup
(74) Attorney, Agent, or Firm—Brezina & Ehrlich

(57) ABSTRACT

A substantially alcohol-free composition for treatment of acne contains about 0.05 to 26% by weight salicylic acid and about 0.05 to 28% by weight of a solubilizing agent for the salicylic acid, which is sodium tetraborate, sodium carbonate or sodium bicarbonate, dissolved in a cosmetically acceptable aqueous medium.

10 Claims, No Drawings

ACNE TREATMENT COMPOSITIONS

BACKGROUND OF THE INVENTION

1. Field of the Invention

The invention relates to the field of over-the-counter type acne treatment compositions.

2. Description of Related Art

Compositions for treatment of acne vulgaris, white heads, black heads and comedones are well known. Generally, such compositions include a keratolytic agent, such as salicylic acid, which dissolves the intracellular matrix of the treated lesion and causes the lesion to slough off the body as dead tissue.

Salicylic acid has been approved by the US Food and Drug Administration for treatment of acne in concentrations of 0.5 to 2% by weight. Such compositions may be in the form of a gel, lotion, cream or solution to be applied with pads.

Salicylic acid is sparingly soluble in water, 1 gram dissolving in about 460 ml of water at room temperature (about 0.2% by weight), to produce a solution with a pH of 2.4. Salicylic acid has a far greater solubility in alcohol, 1 gram dissolving in about 2.7 ml, so most acne treatment compositions are based on a mixture of alcohol and water. The presence of alcohol permits a far greater solubility of salicylic acid than would be possible with water alone. However, alcohol is associated with burning or stinging in many people, so it would be advantageous to provide a salicylic acid composition which is substantially free of alcohol entirely.

SUMMARY OF THE INVENTION

It is therefore an object of the invention to provide a treatment for acne which is formulated without alcohol and other skin irritants.

It is another object of the invention to provide a treatment for acne which is in the form of a clear liquid which can be applied with a pad.

It is a further object of the invention to provide a composition for treating acne which also serves as a facial cleanser.

In order to achieve these and other objects, the invention is directed to an aqueous, substantially alcohol-free composition for treatment of acne comprising salicylic acid solubilized with at least one solubility enhancer selected from the group consisting of sodium tetraborate, sodium bicarbonate and sodium carbonate.

DETAILED DESCRIPTION OF THE INVENTION

The salicylic acid which is the active ingredient of the composition of the invention must be adequately solubilized in the absence of alcohol. The term "alcohol" as used herein refers to the lower alkanols, in particular, methanol, ethanol, propanol and isopropanol.

Salicylic acid occurs in the form of acicular crystals or crystalline powder with a melting point of 157–159° C. and a strong tendency to discolor in sunlight and in the presence of ferric salts. While salicylic acid is only slightly soluble in water, salicylic acid can be solubilized by mixing with sodium tetraborate (borax), sodium carbonate or sodium bicarbonate. The reaction with these solubilizing agents both eliminates the crystalline nature of, the salicylic acid and buffers the resulting solution to any degree desired, so that a product may be prepared which is close to skin pH. Sodium tetraborate is preferred.

Preferably, the salicylic acid and a solubilizing agent are heated to about 45°–50° C. in aqueous mixture until a clear solution is obtained. Best results are achieved by heating with strong agitation. The resulting solution does not recrystallize, even when subjected to several freeze-thaw cycles (−20° to +45° C.), and no color change occurs during such cycles.

The compositions of the invention can contain about 0.1 to 26% by weight salicylic acid, preferably about 0.5 to 20% by weight, and more preferably about 0.5 to 5% by weight. For solubilization, about 0.05 to 28% by weight of one or more solubilizing agents will preferably be used. In order to operate within FDA guidelines for over-the-counter medications, the compositions will contain 0.5 to 2% by weight salicylic acid.

When the salicylic acid is to be formulated into a clear solution as described above for direct application or application with a pad, the salicylic acid and solubilizing agent will be present in a cosmetically acceptable medium, generally containing one or more mild cleansing detergents such as PPG-5-ceteth-20, ammonium xylene sulfonate or ammonium lauryl sulfate, among others. Ammonium xylene sulfonate and ammonium lauryl sulfate are preferred, and are preferably used in combination. Other components of the medium may include natural plant extracts, preservatives and fragrances, citric acid and a chelating agent such as tetrasodium EDTA.

The composition as described may be applied directly to the affected area, or may be applied with a non-woven pad as is well known in the art. In particular, the composition may be dispensed from a container containing one or more non-woven pads which are saturated with the solution.

EXAMPLES

Example 1

A clear solution is prepared with the following composition:

| Component | % by weight |
| --- | --- |
| salicylic acid | 2.0 |
| Sodium tetraborate and/or sodium carbonate and/or sodium bicarbonate | 2.75 |
| citric acid | 0.30 |
| tetrasodium EDTA | 0.10 |
| natural plant extracts | 24.5 |
| Preservative & fragrance | 0.550 |
| Water | QS to 100% |

Example 2

A clear topical solution is prepared with the following composition:

| Component | % by weight |
| --- | --- |
| salicylic acid | 2.0 |
| sodium tetraborate | 2.75 |
| citric acid | 0.36 |

-continued

| Component | % by weight |
| --- | --- |
| tetrasodium EDTA | 0.01 |
| fragrance | 0.1 |
| ammonium xylene sulfonate (40% by weight) | 6.65 |
| ammonium lauryl sulfate | 1.7 |
| DMDM hydantoin (preservative) | 0.40 |
| PPG-5-ceteth-20 | 0.20 |
| menthol | 0.05 |
| simethicone (antifoam) | 0.0440 |
| Water | QS to 100% |

What is claimed is:

1. A non-irritating composition for topical application, comprising, by weight:
   about 0.05 to 26% of salicylic acid,
   about 0.05 to 28% of a salicylic acid solubilizing agent consisting essentially of at least one compound selected from the group consisting of sodium tetraborate, sodium carbonate and sodium bicarbonate, said solubilizing agent being present in an amount sufficient to fully solubilize the salicylic acid in the absence of an alcohol, and
   a cosmetically acceptable aqueous medium in which the salicylic acid and solubilizing agent are dissolved.

2. The composition of claim 1, wherein the salicylic acid is present in an amount of about 0.5 to 2% by weight.

3. The composition of claim 1, wherein the cosmetically acceptable aqueous medium contains at least one surfactant.

4. The composition of claim 3, wherein said at least one surfactant is selected from the group consisting of PPG-5-ceteth-20, ammonium xylene sulfonate, and ammonium lauryl sulfate.

5. The composition of claim 1, wherein the cosmetically acceptable medium contains citric acid.

6. The composition of claim 1, wherein the cosmetically acceptable medium contains a chelating agent.

7. The composition of claim 1, in combination with a non-woven pad as dispensing medium, the pad being saturated with said composition.

8. The composition of claim 1, comprising:

| Component | % by weight |
| --- | --- |
| salicylic acid | 2.0 |
| solubilizing agent | 2.75 |
| citric acid | 0.30 |
| tetrasodium EDTA | 0.10 |
| plant extracts | 24.5 |
| Preservative & fragrance | 0.550 |
| Water | QS to 100%. |

9. The composition of claim 1, comprising:

| Component | % by weight |
| --- | --- |
| salicylic acid | 2.0 |
| sodium tetraborate | 2.75 |
| citric acid | 0.36 |
| tetrasodium EDTA | 0.01 |
| fragrance | 0.1 |
| ammonium xylene sulfonate (40% by weight) | 6.65 |
| ammonium lauryl sulfate | 1.7 |
| DMDM hydantoin (preservative) | 0.40 |
| PPG-5-ceteth-20 | 0.20 |
| menthol | 0.05 |
| simethicone (antifoam) | 0.0440 |
| Water | QS to 100%. |

10. The composition of claim 1, which is alcohol-free.

* * * * *